United States Patent [19]

Hähnle et al.

[11] Patent Number: 5,800,398
[45] Date of Patent: Sep. 1, 1998

[54] METHOD AND APPARATUS FOR POSITIONING OPERATING TUBES

[75] Inventors: Friedrich Hähnle, Bretten; Helmut Heckele, Knittlingen; Uwe Schaumann, Oberderdingen, all of Germany

[73] Assignee: Richard Wolf GmbH, Knittlingen, Germany

[21] Appl. No.: 637,367

[22] Filed: Apr. 25, 1996

[30] Foreign Application Priority Data

Apr. 28, 1995 [DE] Germany .................. 195 15 626.9

[51] Int. Cl.⁶ .................................................. A61M 5/178
[52] U.S. Cl. ............................................................ 604/164
[58] Field of Search .................................. 604/160, 161, 604/164, 165, 166

[56] References Cited

U.S. PATENT DOCUMENTS

| | | | |
|---|---|---|---|
| 1,064,307 | 6/1913 | Fleming | 604/161 X |
| 3,545,443 | 12/1970 | Ansri | 604/160 |
| 4,326,519 | 4/1982 | D'Alo et al. | 604/165 |
| 4,345,596 | 8/1982 | Young | 604/161 X |
| 4,609,370 | 9/1986 | Morrison | 604/165 |
| 4,682,981 | 7/1987 | Suzuki et al. | 604/165 X |
| 4,798,591 | 1/1989 | Okada | 604/165 X |
| 4,966,588 | 10/1990 | Rayman et al. | 604/165 |
| 5,011,478 | 4/1991 | Cope | 604/165 |
| 5,092,846 | 3/1992 | Nishijima et al. | 604/165 |
| 5,261,888 | 11/1993 | Semm | 604/164 |

*Primary Examiner*—Max Hindenburg
*Assistant Examiner*—Pamela L. Wingood
*Attorney, Agent, or Firm*—Cohen, Pontani, Lieberman & Pavane

[57] ABSTRACT

An instrument for positioning operating tubes in endoscopic operations. A distally pointed cannula tube serves as a guiding probe for introduction into a patient's body so that the distal end is disposed closely proximate the operating site, and carries a handle that is removably attached to the cannula tube proximal end. The cannula tube is hollow for receiving therethrough a mandarin. The mandarin and tube handle are removed from the cannula tube once the tube is inserted into the patient's body, thus leaving only the cannula tube extending into the body of the patient to serve as a guiding probe for one or more operating tubes.

14 Claims, 5 Drawing Sheets

1

METHOD AND APPARATUS FOR POSITIONING OPERATING TUBES

BACKGROUND OF THE INVENTION

1. Field of the Invention

The present invention relates to instruments for positioning operating tubes in a patient's body for use in operations, and in particular to an instrument for positioning dilatation tubes in a patient's body for use in endoscopic operations.

2. Description of the Related Art

An instrument known from DE-A-3025785 is employed for the positioning of operating tubes in endoscopic operations, most particularly dilatation tubes used for introducing medical endoscopes into a patient's body to inspect or operate. With this instrument, a sequence of guiding probes, over which the operating tubes can be slidably guided to the operating position, are introduced and positioned partially entering the patient's body. The operating tubes are typically one or more dilatation tubes of increasing diameter that are introduced one after another to serially expand the puncture made by the instrument.

The use of such an instrument in endoscopic intervertebral disc operations (percutaneous endoscopic discectomy) is the subject-matter of U.S. Pat. No. 4,573,448. A thin puncture tube with a mandrin located therein is brought to the operating location with visual guidance provided by X-rays and ultrasound. After reaching the desired location, the mandrin is removed and a guide wire is pushed through the puncture tube. The puncture tube is subsequently removed and a guiding probe is pushed over the guide wire and positioned in the operating area whereupon the guide wire can be removed. One or more dilatation tubes can then be guided, one at a time, over this guiding probe to the operating location, each tube serving as a guide for the next, and this procedure is continued until the access to the operating location has been sufficiently enlarged to permit introduction of an actual instrument tube.

After inserting and correctly placing the instrument tube, the guide wire as well as the guiding probe and the one or more dilatation tubes are pulled out of the instrument tube so that the operating instrument can be introduced into the resulting aperture in the patient's body at the operating location. A similarly designed and operated instrument is also disclosed in WO 93/04652.

The disadvantage of previously known instrumentation is that many different individual steps must be carried out prior to the eventual introduction and placement of the instrument tube. Such procedures are so time consuming that they account for a significant portion of operating time, and thus markedly increase the cost and risk to the patient. Moreover, a large number of different instruments must be at the user's disposal, which accordingly necessitates higher costs in the supply of comprehensive instrumentation.

SUMMARY OF THE INVENTION

The present invention provides an instrument for positioning one or more operating tubes in a patient's body so as to allow the dilatation procedure, up to the positioning of the operating instrument tube, to be achieved with fewer instrument parts than previously known operating tube positioning instruments, thereby considerably reducing the required time and associated costs of the operation.

The instrument of the present invention comprises a pointed cannula tube with a detachable handle and a mandrin which is insertable into the cannula tube through the handle. After the instrument is introduced into a patient's body, the handle and the mandrin are removed, leaving the cannula tube in the body. One or more dilatation tubes may then be slid over the cannula tube to expand the puncture in the patient's body for observation or for insertion of additional instruments.

A particular feature of the instrument of the present invention is that once the instrument is inserted into the patient's body, the mandrin and the handle may be removed, thus enabling the cannula tube to serve as a guiding probe for operating tubes. This is advantageous over previously known instruments in that no additional steps, such as using a guiding wire and inserting a separate guiding probe, are required.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference numerals depict similar elements throughout the several views.

DETAILED DESCRIPTION OF THE PRESENTLY PREFERRED EMBODIMENTS

Figure 1:
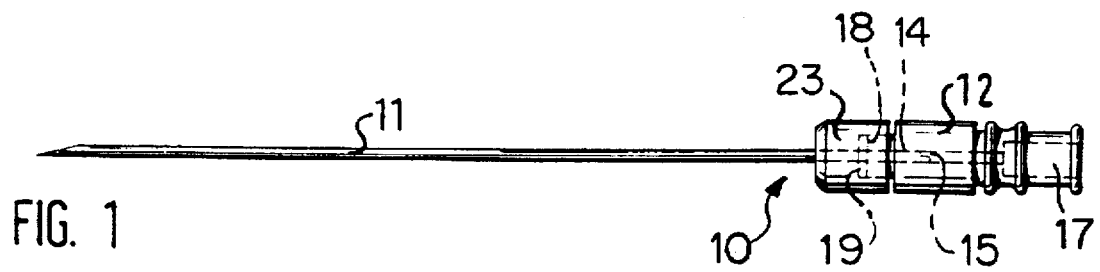
FIG. 1 is a lateral view of a cannula constructed in accordance with the teachings of the present invention with a detachably connected handle at its proximal end.
Figure 2:
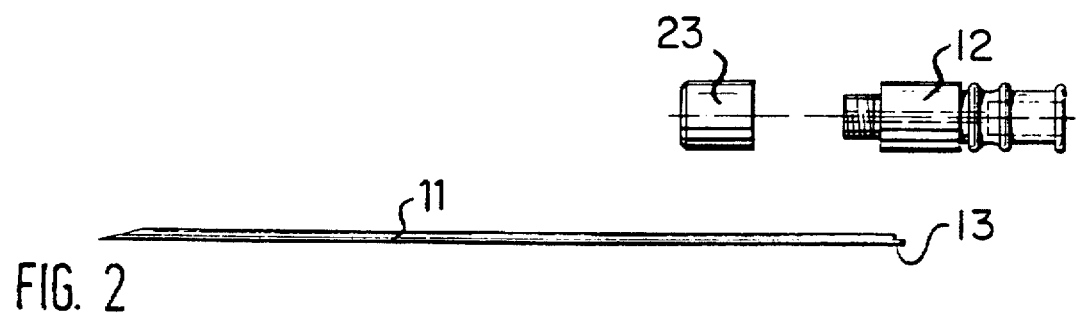
FIG. 2 is a lateral view of the cannula of FIG. 1 showing the handle separated from the cannula and in the dismantled state.
Figure 3:
FIG. 3 is a lateral view of a mandrin for use with the inventive cannula.
Figure 4:
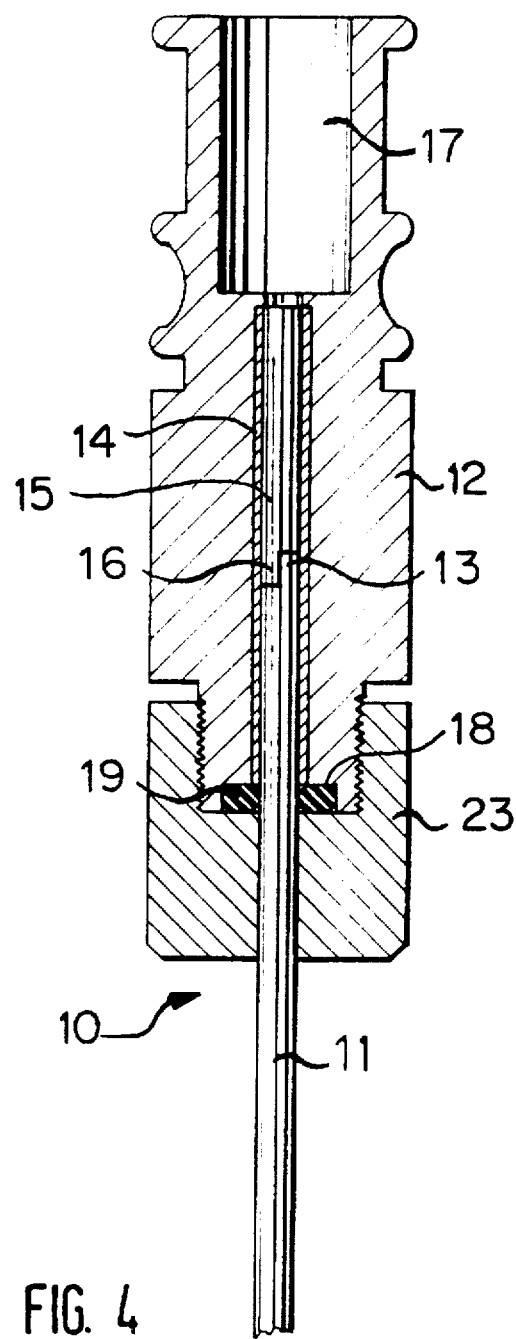
FIG. 4 is an enlarged view of the cannula of FIG. 1 showing a longitudinal section of the handle.
Figure 4:

A currently preferred embodiment of an instrument constructed in accordance with the present invention is shown in FIGS. 1–5 and includes a cannula 10 (FIGS. 1, 2, 4, and 5) and a mandrin 20 (FIGS. 3 and 5) which is guidedly receivable in and through the cannula. Referring to FIGS. 1, 2 and 4, the cannula 10 comprises a hollow cannula tube 11 which is pointed at its distal end and carries a detachable handle 12 at its proximal end. The proximal end of the cannula tube is also provided with a projection 13. The handle 12 has a central longitudinal bore 14 sized for receiving the cannula tube 11. A locking tube 15 of substantially the same diameter as the cannula tube 11 is disposed and secured against relative movement within the central handle bore 14 and includes, at its distal end, a locking section or recess or tab 16 formed to mate with the cannula projection 13 and to provide therewith a rotationally secure engagement of the tube 11 and handle 12. Thus, when the cannula tube 11 is inserted into the handle 12, the projection 13 engages the locking tube tab 16 to prevent rotation of the cannula tube 11 relative to the handle 12. The handle 12 may be additionally be formed so as to include the locking tab 16 or an integral or unitary part of the wall structure forming the handle bore 14, thus obviating the need for a separate locking tube 15 disposed and secured against relative movement within the handle bore 14. The handle 12 also includes at its proximal end a centrally disposed enlarged recess 17 concentric with the central bore 14, and a centrally disposed cutout or hollow 18 concentric to the central bore and sized for receiving an elastic O-ring 19 at its distal end. The distal end of the handle 12 may also have a reduced diameter threaded region.

A threaded union nut 23 guided (by way of example) over and along the cannula tube 11 from its pointed distal end is rotatably engageable with the threads at the distal end of the handle 12, as seen in FIG. 4. As the union nut 23 is rotationally tightened about the threaded handle distal end, the O-ring 19 is compressed around the cannula tube 11 to thereby hold the tube 11 in place and against unintended disengagement from or longitudinal movement relative to the handle 12.

Referring now to FIG. 3, the mandrin 20 carries a mandrin handle 21 secured thereto at its proximal end. The mandrin handle 21 has a diametrically reduced part 22 at its distal end that is sized for receipt within the cannula handle recess 17 when the mandrin 20 is inserted into the cannula 10 through the handle 12.

Figure 5:
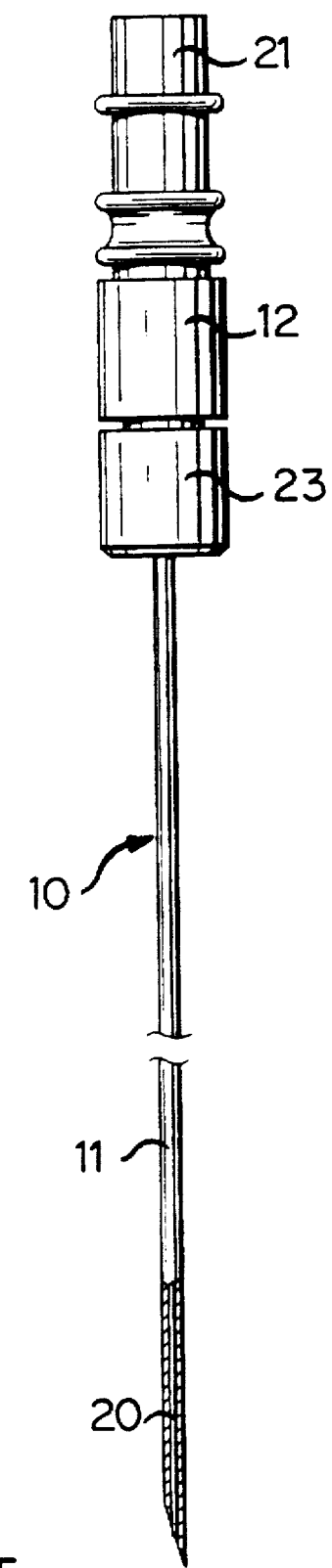
FIG. 5 shows the cannula of FIG. 1 partly in longitudinal section with an inserted guiding probe.

FIG. 5 depicts the fully assembled instrument of the invention with the mandrin 20 inserted into and through the cannula 10.

The instrument of the present invention is particularly useful in the performance of endoscopic intervertebral disc operations. Thus, the following description in conjunction with FIGS. 6–8 describes, by way of example, a typical anticipated and intended use of the inventive instrument in an endoscopic intervertebral disc operation. Those skilled in the art will nevertheless recognize and appreciate that the instrument of the present invention can also be used in other types of endoscopic and like operations which necessitate the use of one or more operating tubes and instrument tubes that must be partially or fully inserted into the patient's body.

Figure 6:
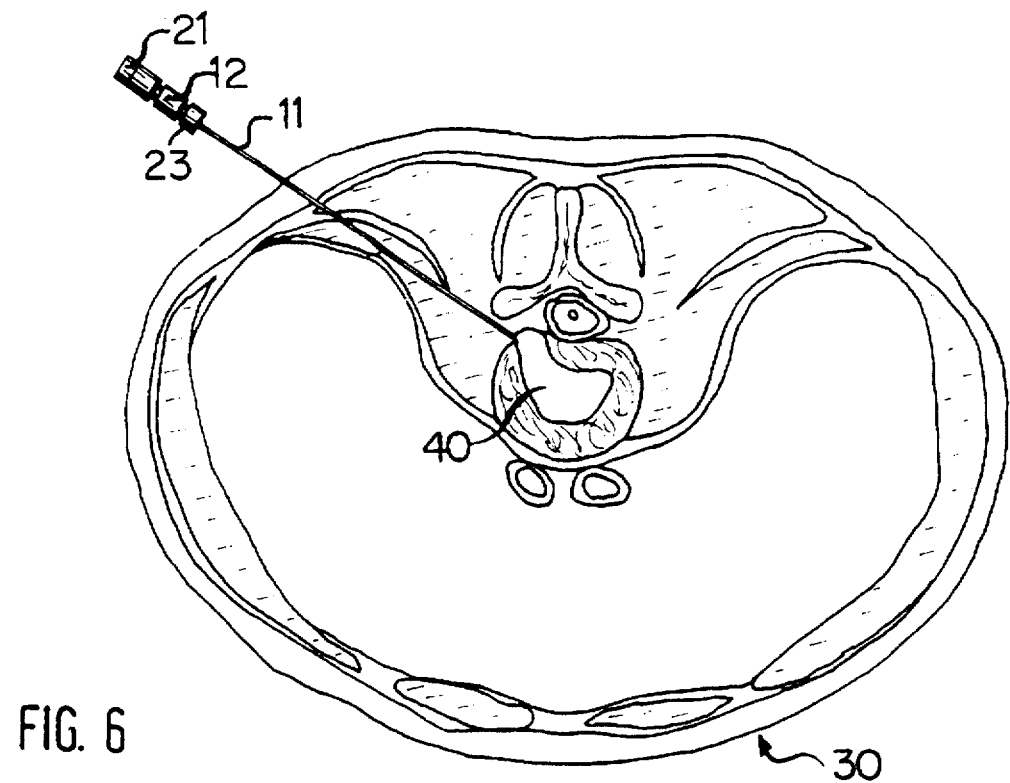
FIG. 6 is a cross-sectional representation of the human body in the region of the abdominal cavity with an introduced cannula with mandrin in the region of an intervertebral disc.
Figure 7:
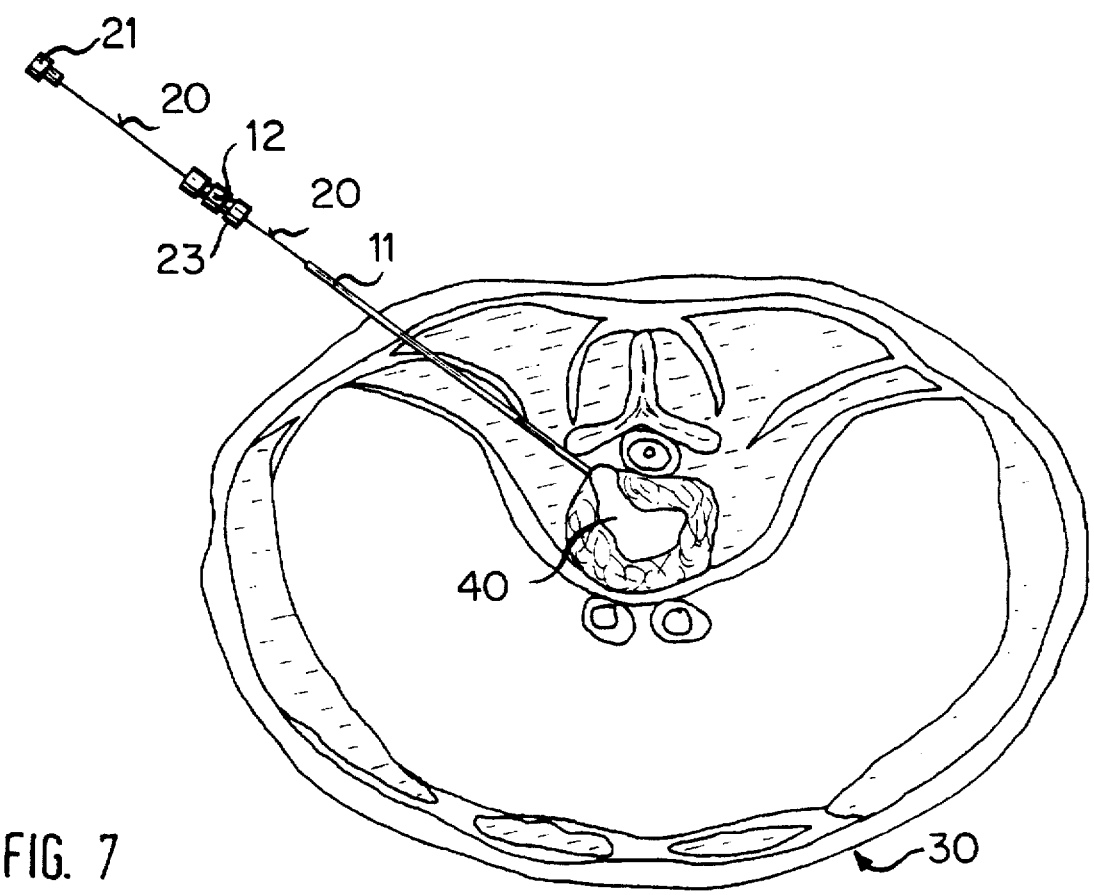
FIG. 7 is a cross-sectional representation similar to FIG. 6 showing the withdrawal of the mandrin from the cannula, leaving the cannula in the body of the patient.
Figure 8:
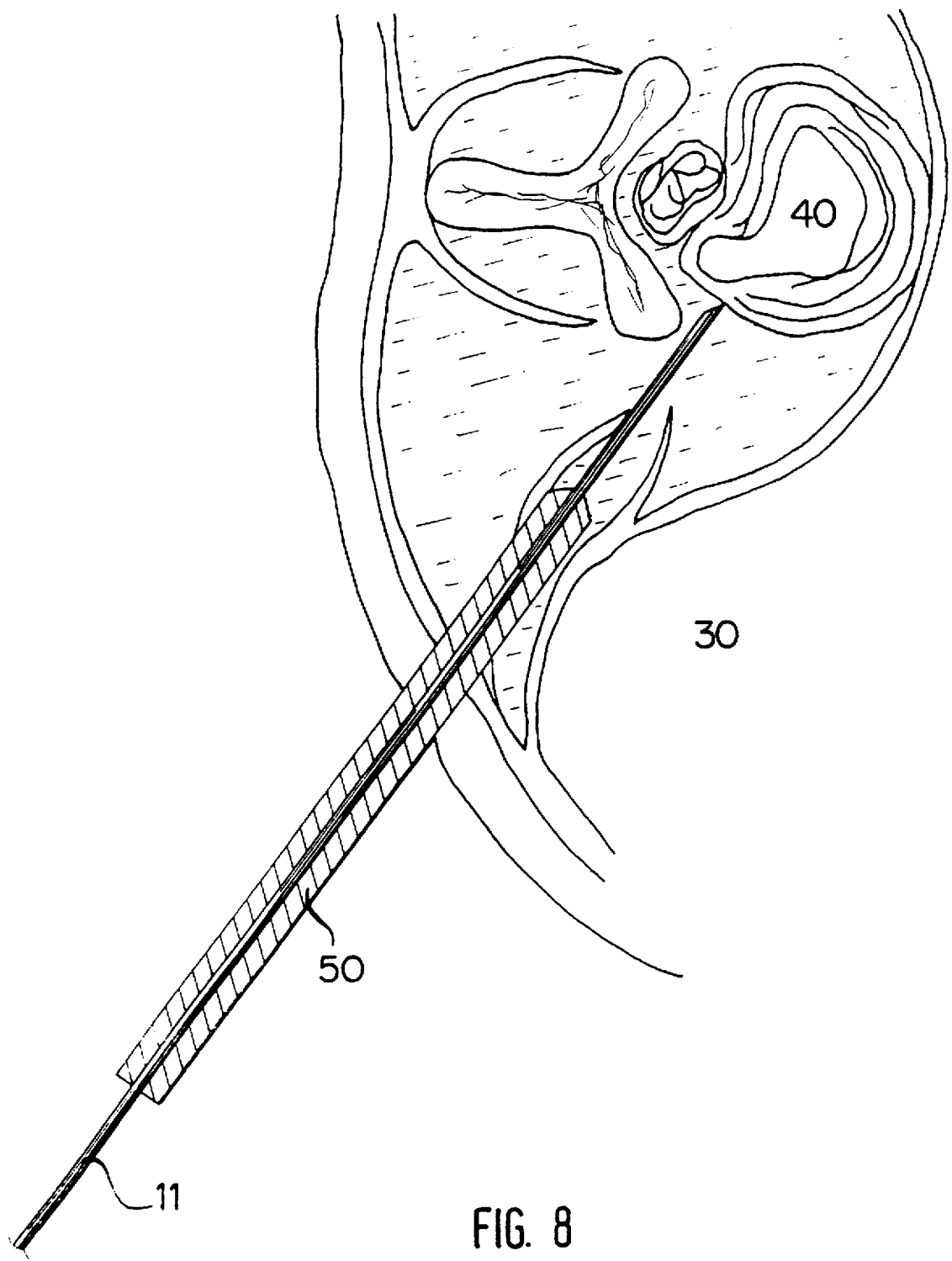
FIG. 8 is an enlarged partial cross-section similar to FIGS. 6 and 7 with the cannula left in the body of the patient and a dilatation tube guidedly advanced over the cannula.

With particular reference, therefore, to FIGS. 6–8, the cannula 10 with the union nut 23 tightly engaging the handle distal end and an inserted mandrin 20 (FIG. 1) is introduced into the body of a patient 30 and, in the example shown, the cannula distal tip is located closely proximate or at an intervertebral disc 40. The union nut 23 is then at least partially unscrewed from the handle 12 to an extent sufficient to release the compression forces or pressure on the O-ring 19. This in turn releases the O-ring 19's compression on the cannula rod 11 so that the mandrin 20, together with the handle 12 and the union nut 23, can then be removed from within and about the cannula tube 11 by proximally pulling on the union nut 23 while the cannula tube 11 remains in the patient's body 30, as shown in FIG. 7. Alternatively, after the union nut 23 is at least partially unscrewed, the mandrin 20 may be removed from within the cannula first, followed by the handle 12 and the union nut 23.

The cannula tube 11 can then serve as a guiding probe in the subsequent dilatation procedure. The dilatation tubes typically used in endoscopic operations are so matched or related one to another with respect to their internal and external diameters that each dilatation tube is slidable over another having a smaller diameter in a concentric or telescoping manner. A one piece dilatator having diametric graduations or conical in cross-section may also be used. Referring specifically to FIG. 8, a first dilatation tube 50 having an internal diameter just larger than the external diameter of the cannula tube 11 is first guidedly moved or pushed over and about the tube 11 until its distal end extends into the patient's body proximate the site or the location of the operation. Additional, increasingly larger dilatation tubes (not shown) may then be pushed or moved over this combination of the cannula tube 11 and dilatation tube(s) 50 in a concentric or telescoping fashion to gradually enlarge the opening into the patient's body to the operating site.

When using several dilatation tubes, this procedure is continued until the puncture channel is sufficiently dilated and widened to enable the operating instrument tube to be introduced guidedly over and along the outermost dilatation tube. With the operating instrument tube then in place, the cannula tube 11 and dilatation tube(s) 50 may be proximally withdrawn or pulled out from within the patient. This allows the site or region of operation to be initially observed, using for example an optical viewing system, and then, after replacing the optical viewing system with an endoscopic operating tool such as a forceps, the operating procedure may be commenced.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. It is the intention, therefore, to be limited only as indicated by the scope of the claims appended hereto.

We claim:

1. An instrument for positioning an operating tube in a patient's body for use in an operation, comprising:

an elongated cannula tube over which an operating tube is slidably guidable to an operating site in a patient's body, said cannula tube having a pointed distal end, a proximal end and a hollow interior;

a handle configured for detachable positioning on the proximal end of said cannula tube;

a mandrin sized for insertion into and through the cannula tube hollow interior through the handle detachably positioned on said cannula tube proximal end and for removal from the cannula tube through said proximal end when the cannula tube is positioned in a patient's body so as to leave the cannula positioned in the patient's body for slidably guiding an operating tube over said cannula tube and into the patient's body to the operating site; and gripping means on said handle operable for releasably retaining said cannula tube against longitudinal displacement of said cannula tube relative to said handle when said handle is positioned on the proximal end of said cannula tube, and engagement means on said cannula tube and said handle for preventing rotational movement of said cannula tube relative to said handle when said handle is positioned on the proximal end of said cannula tube.

2. An instrument in accordance with claim 1, wherein said engagement means comprises a projection on one of said handle and the proximal end of said cannula tube and a recess defined on the other of said handle and the proximal end of said cannula tube for cooperative engagement when said handle is positioned on the proximal end of said cannula tube so as to prevent rotational movement of said cannula tube relative to said handle.

3. An instrument in accordance with claim 2, wherein said handle further comprises a throughbore defined through said handle and in which said cannula tube proximal end is receivable to position said handle on the cannula tube proximal end, and a locking tube disposed in said throughbore and comprising one of said cooperatively engageable projection and recess.

4. An instrument in accordance with claim 1, wherein said handle further comprises a throughbore defined through said handle and in which said cannula tube proximal end is receivable to position said handle on the cannula tube proximal end, and an elastic ring of said handle for elastic deformation against the cannula tube to retain said cannula tube against longitudinal displacement of said cannula tube relative to said handle when said gripping means is operated with the handle positioned on the proximal end of said cannula tube.

5. An instrument in accordance with claim 2, wherein said handle further comprises a throughbore defined through said handle and in which said cannula tube proximal end is receivable to position said handle on the cannula tube proximal end, and an elastic ring of said handle for elastic deformation against the cannula tube to retain said cannula tube against longitudinal displacement of said cannula tube relative to said handle when said gripping means is operated with the handle positioned on the proximal end of said cannula tube.

6. An instrument in accordance with claim 1, wherein said handle comprises a handle body having a threaded end, and wherein said gripping means comprises a nut including threads matable with said handle body threads for rotative engagement of said nut with said handle body to releasably retain said cannula tube against longitudinal displacement of said cannula tube relative to said handle when said handle is positioned on the proximal end of said cannula tube.

7. An instrument in accordance with claim 4, wherein said handle comprises a handle body having a threaded end, and wherein said gripping means comprises a nut including threads matable with said handle body threads for rotative engagement of said nut with said handle body to elastically deform said ring about the cannula tube for releasably retaining said cannula tube against longitudinal displacement of said cannula tube relative to said handle when said handle is positioned on the proximal end of said cannula tube.

8. An instrument in accordance with claim 7, wherein said handle body carries said elastic ring at said handle body threaded end for elastic deformation of said ring when the nut is rotatively engaged with the handle body to operate said gripping means.

9. An instrument in accordance with claim 2, wherein said projection is defined on the proximal end of said cannula tube and said recess is defined on said handle.

10. An instrument in accordance with claim 3, wherein said projection is defined on the proximal end of said cannula tube and said recess is defined on said locking tube.

11. A method for positioning an operating tube in a patient's body for use in an operation, comprising the steps of:

detachably positioning, on an elongated cannula tube having a pointed distal end, a proximal end and a hollow interior, a handle having an interior throughbore by inserting the proximal end of the cannula tube into the throughbore to position the handle on the cannula tube proximal end and operating a gripping means of the handle to releasably retain the cannula tube against longitudinal displacement of the cannula tube relative to the handle;

inserting into and through the cannula tube hollow interior and handle throughbore a mandrin sized for receipt in the hollow interior and throughbore;

introducing the cannula tube distal end into a patient's body with the handle detachably positioned on the cannula tube proximal end and the mandrin inserted into and through the cannula tube hollow interior and handle throughbore by advancing the cannula tube pointed distal end through an entry location of the patient's body until the cannula tube distal end is disposed proximate an intended operating site in the patient's body;

releasing the gripping means to release the retention of the introduced cannula tube against longitudinal displacement relative to the handle while the cannula tube distal end remains disposed proximate the intended operating site in the patient's body;

removing the handle, after said step of releasing the gripping means, from its position on the introduced cannula tube by displacing the handle longitudinally along and relative to the cannula tube in a direction away from the distal end of the cannula tube and the patent's body to thereby separate the handle from the cannula lube while leaving the cannula tube distal end disposed proximate the intended operating site in the patient's body;

removing the inserted mandrin, after said step of introducing the cannula tube distal end, from the cannula tube hollow interior by withdrawing the mandrin through the cannula tube proximal end while leaving the cannula tube distal end disposed proximate the intended operating site in the patients body; and introducing an operating tube into the patient's body lo the operating site by slidably guiding the operating tube over the inserted cannula tube from which the handle has been separated and removed and the mandrin has been withdrawn.

12. A method in accordance with claim 11, wherein said steps of removing the handle and removing the mandrin are carried out simultaneously so that only the cannula tube over which an operating tube is slidably guidable to the operating site remains.

13. A method in accordance with claim 11, wherein said step of detachably positioning the handle on the cannula tube proximal end further comprises longitudinally advancing the cannula tube proximal end into the handle throughbore until a projection defined on one of the cannula tube proximal end and the handle engages a recess defined on the other of the cannula tube proximal end and the handle so as to prevent rotation of the cannula tube relative to the handle when the handle is positioned on the cannula tube proximal end.

14. A method in accordance with claim 11, wherein said step of removing the inserted mandrin further comprises withdrawing the mandrin through the cannula tube proximal end and the handle while leaving the cannula tube distal end disposed proximate the intended operating site in the patient's body.

* * * * *